US012434074B2

(12) United States Patent
Baba

(10) Patent No.: US 12,434,074 B2
(45) Date of Patent: Oct. 7, 2025

(54) NEUTRON RAY THERAPY FACILITY INCLUDING A NEUTRON RAY GENERATING APPARATUS

(71) Applicant: SUMITOMO HEAVY INDUSTRIES, LTD., Tokyo (JP)

(72) Inventor: Tatsuo Baba, Yokosuka (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 203 days.

(21) Appl. No.: 18/474,225

(22) Filed: Sep. 26, 2023

(65) Prior Publication Data

US 2024/0017091 A1 Jan. 18, 2024

Related U.S. Application Data

(63) Continuation of application No. PCT/JP2022/014060, filed on Mar. 24, 2022.

(30) Foreign Application Priority Data

Mar. 30, 2021 (JP) ................................ 2021-057346

(51) Int. Cl.
*A61N 5/10* (2006.01)
*H05H 3/06* (2006.01)

(52) U.S. Cl.
CPC ............ *A61N 5/1078* (2013.01); *A61N 5/10* (2013.01); *A61N 5/1077* (2013.01); *H05H 3/06* (2013.01);
(Continued)

(58) Field of Classification Search
CPC ...... A61N 5/10; A61N 5/1077; A61N 5/1078; A61N 2005/109; A61N 2005/1094; A61N 2005/1087; H05H 3/06
(Continued)

(56) References Cited

U.S. PATENT DOCUMENTS 5,870,447 A * 2/1999 Powell ..................... H05H 3/06 376/190
7,394,081 B2 * 7/2008 Okazaki .................. G21G 1/10 376/190

(Continued)

FOREIGN PATENT DOCUMENTS

JP 2005-283137 A 10/2005
JP 2016-136499 7/2016
JP 2020-146119 9/2020

OTHER PUBLICATIONS

International Search Report of PCT/JP2022/014060, mailed on Jun. 7, 2022.

(Continued)

*Primary Examiner* — Allen C. Ho
(74) *Attorney, Agent, or Firm* — WTA IP Law P.C.

(57) ABSTRACT

A neutron ray generating apparatus includes: an accelerator that emits a particle beam; a target disposition portion that disposes a target that is irradiated with the particle beam to generate a neutron ray; and a transport path that transports the particle beam between the accelerator and the target disposition portion. The target disposition portion and the accelerator are disposed on a reference line of the transport path. A first shield member that shields radiation and a second shield member that shields the radiation and that is disposed to be spaced apart from the first shield member toward an accelerator side are provided between the target disposition portion and the accelerator.

12 Claims, 6 Drawing Sheets

(52) U.S. Cl.
CPC .................. *A61N 2005/109* (2013.01); *A61N 2005/1094* (2013.01)

(58) Field of Classification Search
USPC .......... 250/396 R, 397, 398, 396 ML, 492.3; 378/65
See application file for complete search history.

(56) References Cited

U.S. PATENT DOCUMENTS

| | | | | |
|---|---|---|---|---|
| 8,779,393 | B2 * | 7/2014 | Sasai | A61N 5/1081 250/492.1 |
| 9,789,340 | B2 * | 10/2017 | Liu | A61N 5/1077 |
| 9,889,320 | B2 * | 2/2018 | Liu | A61N 5/1077 |
| 10,082,587 | B1 * | 9/2018 | Akabori | G01T 7/00 |
| 10,155,123 | B2 * | 12/2018 | Mukawa | A61N 5/1077 |
| 10,157,693 | B2 * | 12/2018 | Liu | A61N 5/10 |
| 10,328,286 | B2 * | 6/2019 | Liu | A61N 5/1077 |
| 10,434,333 | B2 * | 10/2019 | Liu | A61N 5/1077 |
| 10,441,815 | B2 * | 10/2019 | Akabori | A61N 5/1048 |
| 10,537,750 | B2 * | 1/2020 | Liu | A61N 5/1049 |
| 10,568,964 | B2 * | 2/2020 | Yamaguchi | A61N 5/1049 |
| 10,639,499 | B2 * | 5/2020 | Liu | A61N 5/1078 |
| 10,773,104 | B2 * | 9/2020 | Liu | A61N 5/1077 |
| 10,791,618 | B2 * | 9/2020 | Hsueh Liu | H05H 3/06 |
| 10,898,731 | B2 * | 1/2021 | Liu | A61N 5/1077 |
| 10,898,733 | B2 * | 1/2021 | Liu | A61N 5/1081 |
| 10,926,108 | B2 * | 2/2021 | Liu | A61N 5/1077 |
| 10,926,110 | B2 * | 2/2021 | Liu | A61N 5/1077 |
| 11,058,898 | B2 * | 7/2021 | Liu | A61N 5/1077 |
| 11,198,023 | B2 * | 12/2021 | Chen | A61N 5/1077 |
| 11,246,209 | B2 * | 2/2022 | Sasai | A61N 5/1077 |
| 11,266,859 | B2 * | 3/2022 | Liu | A61N 5/1077 |
| 11,338,155 | B2 * | 5/2022 | Hsiao | A61N 5/1077 |
| 11,375,602 | B2 * | 6/2022 | Mezei | H05H 3/06 |
| 11,400,314 | B2 * | 8/2022 | Hsiao | A61N 5/1067 |
| 11,400,316 | B2 * | 8/2022 | Liu | A61N 5/10 |
| 11,458,336 | B2 * | 10/2022 | Tsai | A61N 5/1064 |
| 11,559,705 | B2 * | 1/2023 | Chen | A61N 5/1077 |
| 11,561,308 | B2 * | 1/2023 | Liu | A61N 5/1075 |
| 11,583,701 | B2 * | 2/2023 | Liu | A61N 5/1077 |
| 11,740,370 | B2 * | 8/2023 | Liu | A61N 5/1048 250/391 |
| 11,813,483 | B2 * | 11/2023 | Liu | A61N 5/1078 |
| 11,826,583 | B2 * | 11/2023 | Jiang | A61N 5/1078 |
| 11,986,679 | B2 * | 5/2024 | Liu | A61B 6/0407 |
| 12,011,615 | B2 * | 6/2024 | Chen | A61N 5/1077 |
| 12,023,524 | B2 * | 7/2024 | Chen | A61N 5/1078 |
| 12,172,031 | B2 * | 12/2024 | Chen | A61N 5/1039 |
| 12,296,192 | B2 * | 5/2025 | Chen | A61N 5/1071 |
| 12,296,199 | B2 * | 5/2025 | Jiang | A61N 5/1077 |
| 12,303,713 | B2 * | 5/2025 | Kusuoka | A61N 5/1048 |
| 12,324,934 | B2 * | 6/2025 | Liu | A61N 5/1048 |
| 12,383,766 | B2 * | 8/2025 | Zhong | A61N 5/1048 |
| 2005/0242276 | A1 | 11/2005 | Okazaki et al. | |

OTHER PUBLICATIONS

Yoshie Otake, Compact Neutron Systems Expand in Applications—Riken Rans—, J. Particle Accelerator Society of Japan, vol. 13, No. 4, 2016, pp. 229-233, Japan (With English Abstract).

Guang Hu et al., New shielding material development for compact accelerator-driven neutron source, AIP Advances 7, 045213 pp. 1-8, Apr. 21, 2017.

* cited by examiner

NEUTRON RAY THERAPY FACILITY INCLUDING A NEUTRON RAY GENERATING APPARATUS

CROSS-REFERENCE TO RELATED APPLICATIONS

This is a bypass continuation of International PCT Application No. PCT/JP2022/014060, filed on Mar. 24, 2022, which claims priority to Japanese Patent Application No. 2021-057346, filed on Mar. 30, 2021, which are incorporated by reference herein in their entirety.

BACKGROUND

Technical Field

Certain embodiments of the present disclosure relate to a neutron ray generating apparatus and a neutron ray therapy facility.

Description of Related Art

Boron neutron capture therapy (BNCT) using a boron compound is known as a neutron capture therapy that irradiates a cancer cell with a neutron ray to kill the cancer cells. In the boron neutron capture therapy, boron incorporated into the cancer cell in advance is irradiated with the neutron ray, and the cancer cell is selectively destroyed by scattering of heavy charged particles generated by the irradiation.

For example, a neutron ray generating apparatus disclosed in the related art is used to generate a neutron ray used for the therapy described above. The neutron ray generating apparatus disclosed in the related art greatly bends a particle beam generated by an accelerator, using a bending electromagnet, and transports the particle beam to a target of a target disposition portion.

SUMMARY

According to an embodiment of the present disclosure, there is provided a neutron ray generating apparatus including: an accelerator that emits a particle beam; a target disposition portion that disposes a target that is irradiated with the particle beam to generate a neutron ray; and a transport path that transports the particle beam between the accelerator and the target disposition portion. The target disposition portion and the accelerator are disposed on a reference line of the transport path. A first shield member that shields radiation and a second shield member that shields the radiation and that is disposed to be spaced apart from the first shield member toward an accelerator side are provided between the target disposition portion and the accelerator.

According to another embodiment of the present disclosure, there is provided a neutron ray therapy facility including: an accelerator that emits a particle beam; a target disposition portion that disposes a target that is irradiated with the particle beam to generate a neutron ray; and a transport path that transports the particle beam between the accelerator and the target disposition portion. The accelerator and the target disposition portion are disposed on a reference line of the transport path. A first shield member that shields radiation and a second shield member that shields the radiation and that is disposed to be spaced apart from the first shield member toward an accelerator side are provided between the target disposition portion and the accelerator.

DETAILED DESCRIPTION

Here, in such a configuration, the accelerator needs to be disposed such that the emission of the particle beam of the accelerator and the target disposition portion are perpendicular to each other. The present inventors have recognized that in this case, the entirety of the neutron ray generating apparatus becomes large due to a layout relationship between the accelerator and a transport path for the particle beam. On the other hand, when the accelerator is disposed such that the transport path becomes a straight line, there is a possibility that the accelerator is radioactivated due to the influence of radiation leaking from the target.

Accordingly, it is desirable to provide a neutron ray generating apparatus and a neutron ray therapy facility that can be reduced in size while suppressing radioactivation of an accelerator.

Figure 6:
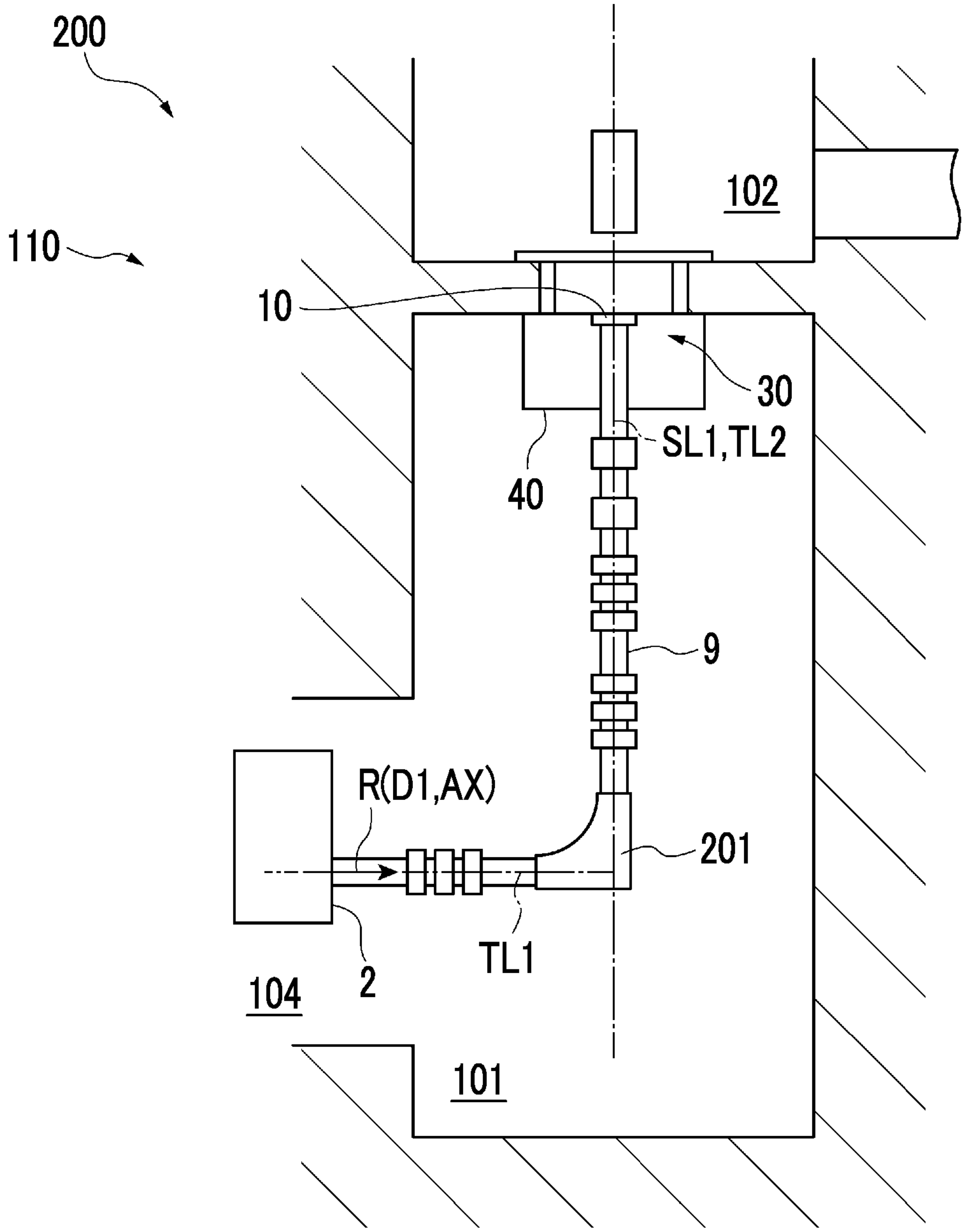
FIG. 6 is a schematic view showing a neutron ray therapy facility according to a comparative example.

In the neutron ray generating apparatus according to the present disclosure, the target disposition portion and the accelerator are disposed on the reference line of the transport path. In such disposition, the size of the entirety of the apparatus can be reduced compared to disposition in which the trajectory of the particle beam from the accelerator is greatly bent as shown in FIG. 6 to irradiate the target with the particle beam. In addition, the first shield member that shields the radiation and the second shield member that shields the radiation and that is disposed to be spaced apart from the first shield member toward the accelerator side are provided between the target disposition portion and the accelerator. In this case, the second shield member can shield the radiation from the target that cannot be completely shielded by the first shield member. For that reason, even when the accelerator is disposed as described above, the radiation toward the accelerator can be shielded by the second shield member. As described above, the size can be reduced while suppressing radioactivation of the accelerator.

The transport path may include a first portion closer to the target disposition portion than to the accelerator, and a reference line of the first portion may overlap the accelerator. In this case, the radiation can be effectively shielded.

A connecting part between the transport path and the accelerator may be disposed to overlap the reference line. In this case, the particle beam emitted from the connecting part of the accelerator can travel straight toward the target along the reference line.

The second shield member may be movable or removable with respect to an installation position. In this case, since the second shield member is movable or removable from the installation position during maintenance, maintainability around the installation positions is improved.

The accelerator may emit the particle beam using a radio frequency. In this case, since different types of particles are less likely to be mixed into the particle beam, the quality of the neutron ray with which an irradiation target is irradiated can be improved. In addition, the need for a bending electromagnet or the like for sorting different types of particles can be eliminated.

The second shield member may be disposed at a position closer to the accelerator between the target disposition portion and the accelerator to locally protect the accelerator. In this case, the second shield member can locally protect the accelerator by narrowing down a range to be protected in the accelerator. Accordingly, the certainty of protection can be improved with a small amount of the shield material.

The second shield member may be disposed at a position closer to the target disposition portion between the target disposition portion and the accelerator. In this case, the second shield member can shield radiation leaking from the first shield member in a preliminary stage before the radiation spreads in a chamber.

According to the neutron ray therapy facility, the same actions and effects as those of the neutron ray generating apparatus described above can be obtained.

Hereinafter, a preferred embodiment of the present disclosure will be described in detail with reference to the drawings.

Figure 1:
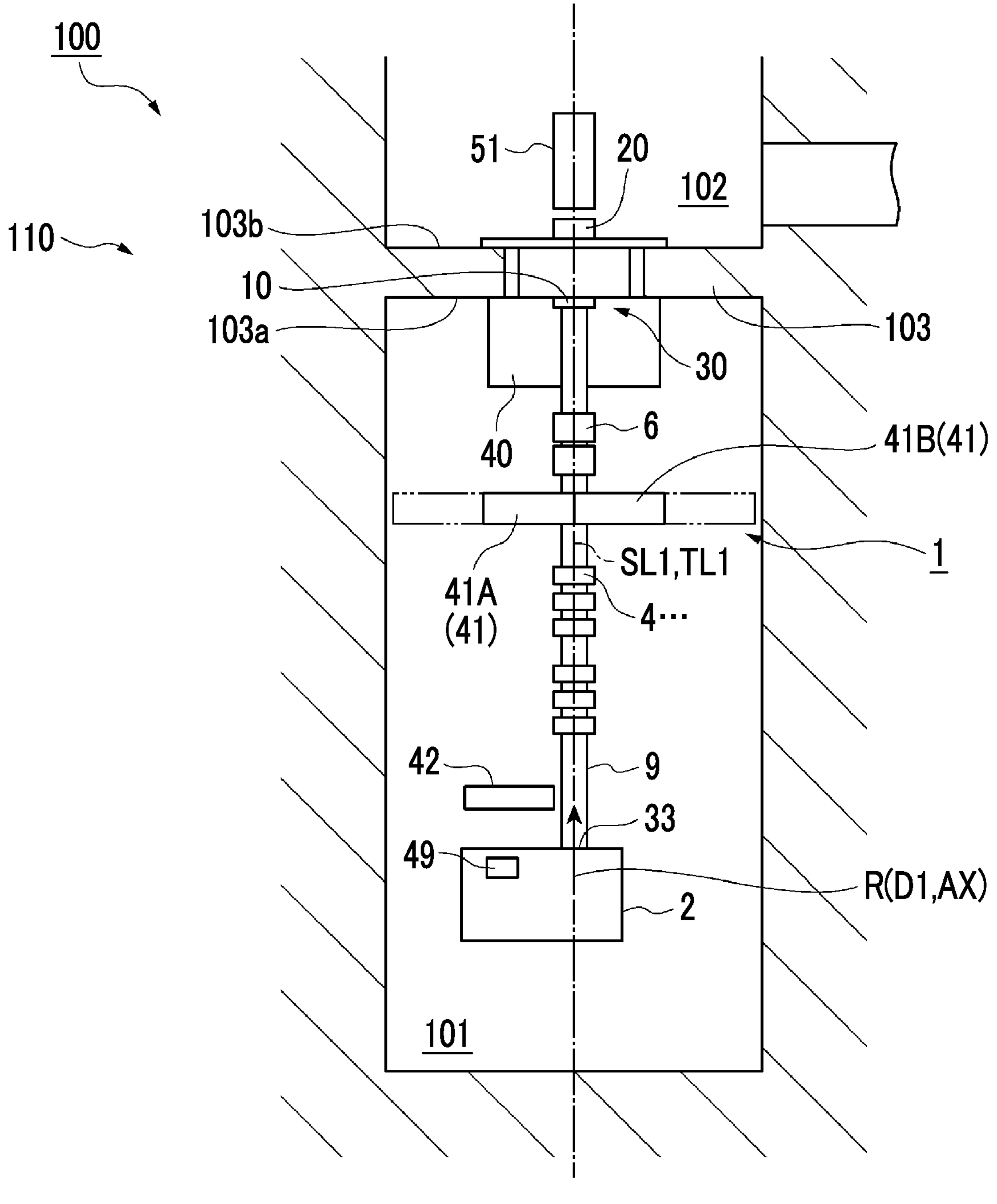
FIG. 1 is a schematic view showing a neutron ray therapy facility including a neutron ray generating apparatus according to an embodiment of the present disclosure.
Figure 2:
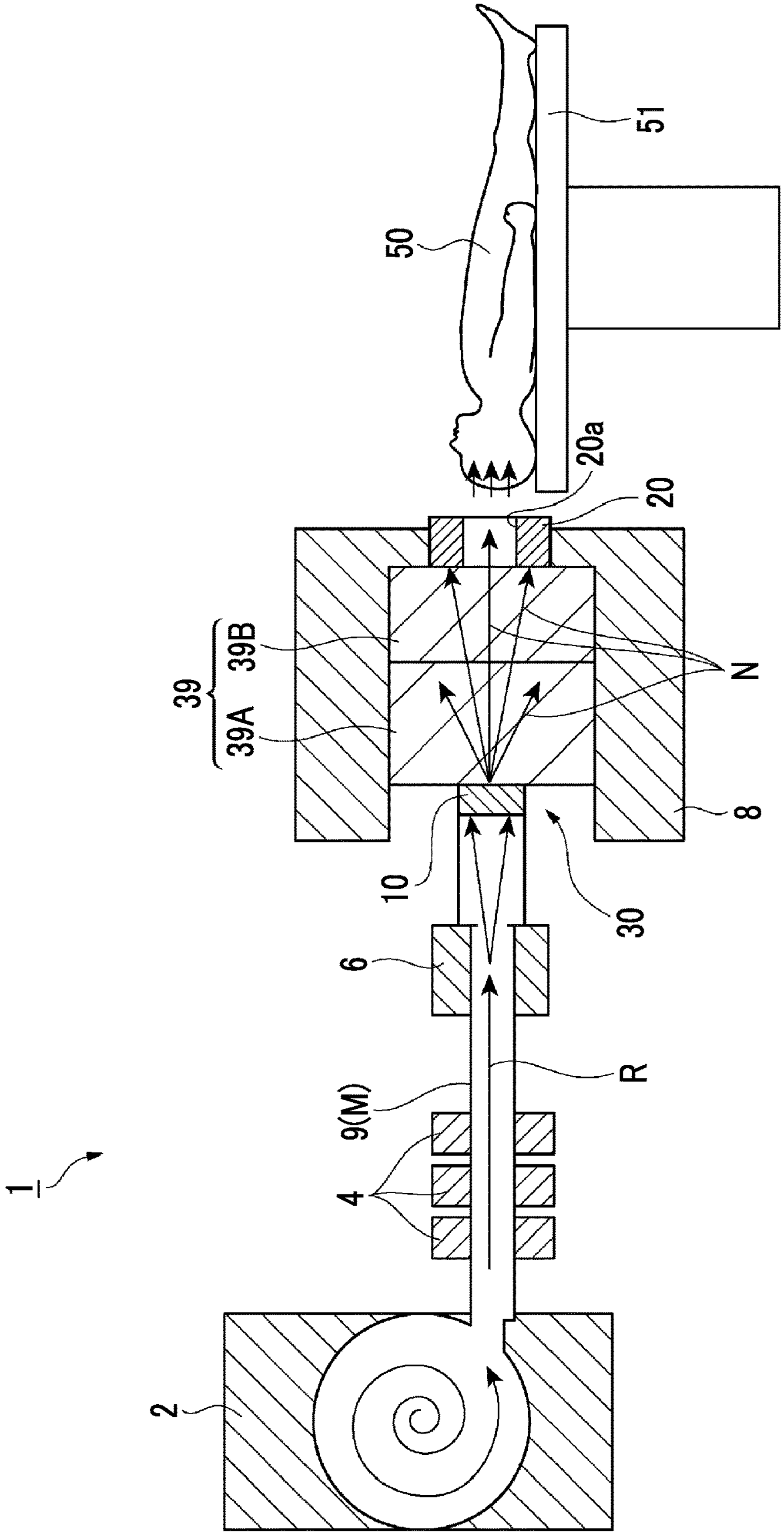
FIG. 2 is a schematic view showing the neutron ray generating apparatus according to the embodiment of the present disclosure.

FIG. 1 is a schematic view showing a neutron ray therapy facility 100 including a neutron ray generating apparatus 1 according to an embodiment of the present disclosure. FIG. 2 is a schematic view showing the neutron ray generating apparatus 1 according to the embodiment of the present disclosure. The neutron ray generating apparatus 1 is used as a neutron capture therapy apparatus that performs cancer treatment using a boron neutron capture therapy (BNCT). First, a configuration of the neutron ray generating apparatus 1 functioning as a neutron capture therapy apparatus will be described with reference to FIG. 2. For example, the neutron ray generating apparatus 1 irradiates a tumor of a patient 50 positioned on a treatment bed 51, to which boron (10B) is administered, with a neutron ray N.

The neutron ray generating apparatus 1 includes an accelerator 2. The accelerator 2 accelerates particles, and emits a particle beam R. It is preferable that the accelerator 2 emits the particle beam R using a radio frequency. Namely, it is preferable that as the accelerator 2, an alternating current (AC) accelerator is adopted rather than a direct current (DC) accelerator such as an electrostatic ("single-ended" or "tandem") accelerator. For example, a cyclotron, a linear accelerator, or the like may be adopted as the accelerator 2.

The particle beam R emitted from the accelerator 2 passes through a transport path 9 referred to as a beam duct of which the inside is kept vacuum and through which the beam can pass, and is transported to a target disposition portion 30. The target disposition portion 30 is a portion that disposes a target 10, and has a mechanism that holds the target 10 so as to assume an irradiation posture. The target disposition portion 30 disposes the target 10 at a position facing an end portion (emission port) of the transport path 9. The particle beam R emitted from the accelerator 2 passes through the transport path 9, and advances toward the target disposed at the end portion of the transport path 9. A plurality of electromagnets 4 (quadrupole electromagnets or the like) and a scanning electromagnet 6 are provided along the transport path 9. The plurality of electromagnets 4 adjust a beam axis of the particle beam R, for example, using electromagnets.

The scanning electromagnet 6 scans the particle beam R, and controls irradiation of the target 10 with the particle beam R. The scanning electromagnet 6 controls the irradiation position of the particle beam R with respect to the target 10.

The neutron ray generating apparatus 1 generates the neutron ray N by irradiating the target 10 with the particle beam R, and emits the neutron ray N toward the patient 50. The neutron ray generating apparatus 1 includes the target 10, a shield member 8, a deceleration member 39, and a collimator 20.

The target 10 is irradiated with the particle beam R to generate the neutron ray N. The target 10 is a solid member made of a material that generates the neutron ray N when irradiated with the particle beam R. Specifically, the target 10 is made of, for example, beryllium (Be), lithium (Li), tantalum (Ta), or tungsten (W), and has, for example, a disk-shaped solid form having a diameter of 160 mm. The target 10 is not limited to a disk shape, and may have another shape.

The deceleration member 39 decelerates the neutron ray N generated by the target 10 (decreases the energy of the neutron ray N). The deceleration member 39 may have a laminated structure including a layer 39A that mainly decelerates fast neutrons contained in the neutron ray N, and a layer 39B that mainly decelerates epithermal neutrons contained in the neutron ray N.

The shield member 8 shields the generated neutron ray N, a gamma ray generated along with the generation of the neutron ray N, and the like so as not to be released to the outside. The shield member 8 is provided to surround the deceleration member 39. An upper portion and a lower portion of the shield member 8 extend to an upstream side of the particle beam R from the deceleration member 39.

The collimator 20 shapes the irradiation field of the neutron ray N, and includes an opening 20*a* through which the neutron ray N passes. The collimator 20 is, for example, a block-shaped member including the opening 20*a* at the center.

Next, a configuration of the neutron ray generating apparatus 1 in the neutron ray therapy facility 100 will be described with reference to FIG. 1. The neutron ray therapy facility 100 is configured by providing the neutron ray generating apparatus 1 inside a building 110. The neutron ray therapy facility 100 mainly includes an accelerator chamber 101 for disposing the accelerator 2 and the transport path 9, and an irradiation chamber 102 for irradiating the patient 50 with the neutron ray N. The accelerator chamber 101 and the irradiation chamber 102 are spaces partitioned off by walls such as concrete. The accelerator chamber 101 and the irradiation chamber 102 are separated from each other by a partition wall 103 of the building 110. The target disposition portion 30 that disposes the target 10 described above is provided in the vicinity of a wall surface 103*a* on an accelerator chamber 101 side of the partition wall 103. The collimator 20 described above is provided on a wall surface 103*b* on an irradiation chamber 102 side of the partition wall 103.

The accelerator 2 is provided at a position spaced apart from the partition wall 103 in the accelerator chamber 101.

Here, in order to a positional relationship between the accelerator 2, the transport path 9, the target 10, and the target disposition portion 30, various terms will be described.

First, a direction in which the accelerator 2 emits the particle beam R is referred to as an "emission direction D1". An irradiation axis AX of the particle beam R emitted from the accelerator 2 in the emission direction D1 is set. The irradiation axis AX is a center line set for the particle beam R at a connecting part 33 between the accelerator 2 and the transport path 9. A reference line SL1 is a center axis of the transport path 9. The reference line SL1 may coincide with a center axis of the target 10 when the target 10 having a disk shape is disposed on the target disposition portion 30.

In the present embodiment, the target 10 and the target disposition portion 30 are disposed at a position facing the accelerator 2 in the emission direction D1. In this case, the accelerator 2 is disposed on the reference line SL1 of the transport path 9. The reference line SL1 of the transport path 9 is, for example, a center axis of the cylinder of a cylindrical vacuum duct forming a part of the transport path. The accelerator 2 can be disposed in a direction in which the cylindrical vacuum duct extends.

Figure 3A:
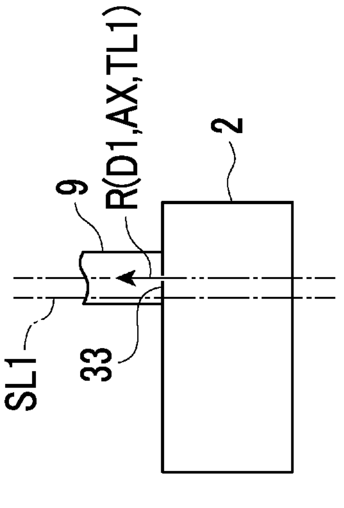
FIGS. 3A to 3F are conceptual views for describing a positional relationship between a reference line and each of an accelerator and a target disposition portion.
Figure 3B:
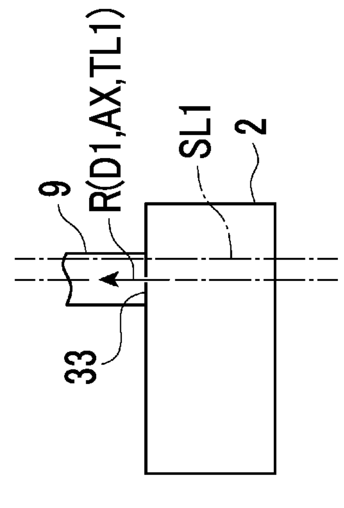
Figure 3C:
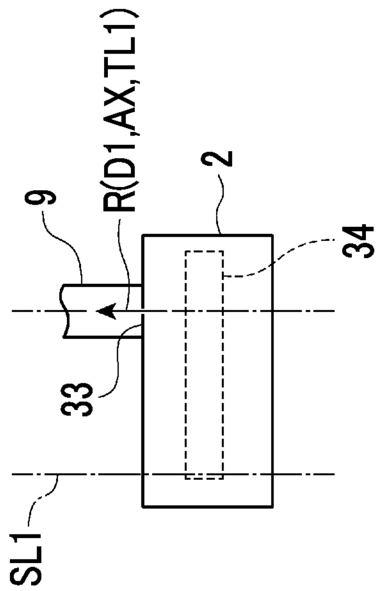
Figure 3D:
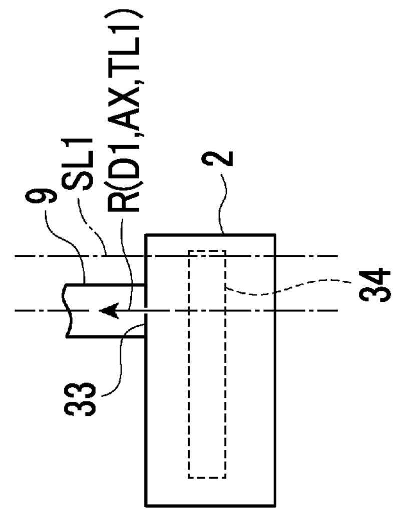
Figure 3E:
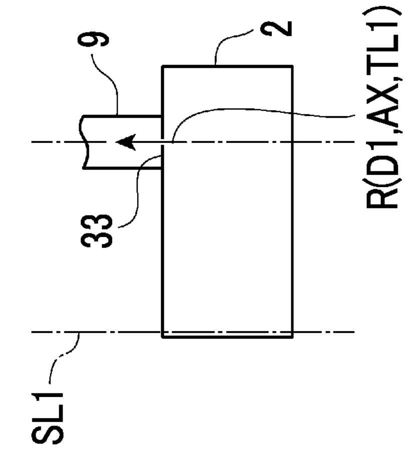
Figure 3F:
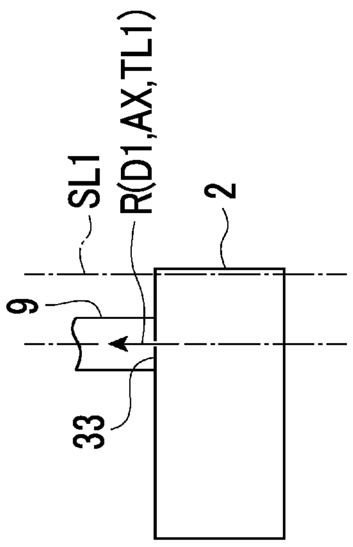

A state where the accelerator 2 is disposed on the reference line SL1 will be described with reference to FIGS. 3A to 3F. FIGS. 3A to 3F are conceptual views describing a mode in which the accelerator 2 and the reference line SL1 overlap each other. As shown in FIGS. 3E and 3F, at least any part of the accelerator 2 may be disposed to overlap the reference line SL1. FIG. 3E shows a state where the reference line SL1 overlaps a boundary portion on one side of the accelerator 2. FIG. 3F shows a state where the reference line SL1 overlaps a boundary portion on the other end side of the accelerator 2. More preferably, as shown in FIGS. 3C and 3D, an acceleration space 34 of the accelerator 2 may be disposed to overlap the reference line SL1. FIG. 3C shows a state where the reference line SL1 overlaps a boundary portion on the one side of the acceleration space 34. FIG. 3D shows a state where the reference line SL1 overlaps a boundary portion on the other end side of the acceleration space 34. More preferably, as shown in FIGS. 3A and 3B, the connecting part 33 of the accelerator 2 with the transport path 9 may be disposed to overlap the reference line SL1. FIG. 3A shows a state where the reference line SL1 overlaps a boundary portion on the one side of the connecting part 33. FIG. 3B shows a state where the reference line SL1 overlaps a boundary portion on the other end side of the connecting part 33.

In the example shown in FIG. 1, a state where the connecting part 33 overlaps the reference line SL1 is shown, particularly, the irradiation axis AX of the particle beam R coincides with the reference line SL1. However, as shown in each figure of FIGS. 3A to 3F, the irradiation axis AX of the particle beam R may not necessarily coincide with the reference line SL1. In addition, describing the positional relationship of the target 10 with reference to the accelerator 2, the target 10 disposed on the target disposition portion 30 may be disposed on the irradiation axis AX of the particle beam R emitted from the accelerator 2. In this case, the connecting part 33 of the accelerator 2 and the target 10 have a positional relationship such that the connecting part 33 and the target 10 face each other in the emission direction D1 while being spaced apart from each other in the emission direction D1.

Figure 4A:
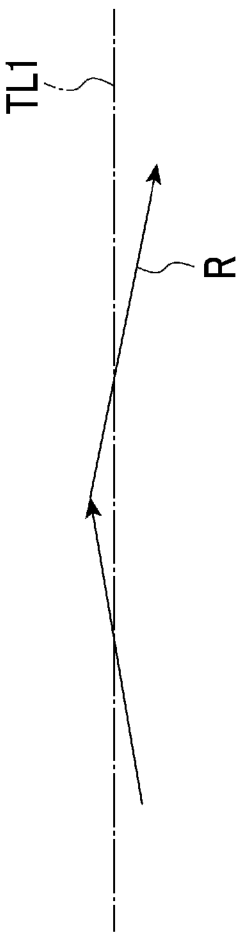
FIGS. 4A to 4C are views for describing a reference trajectory.
Figure 4B:
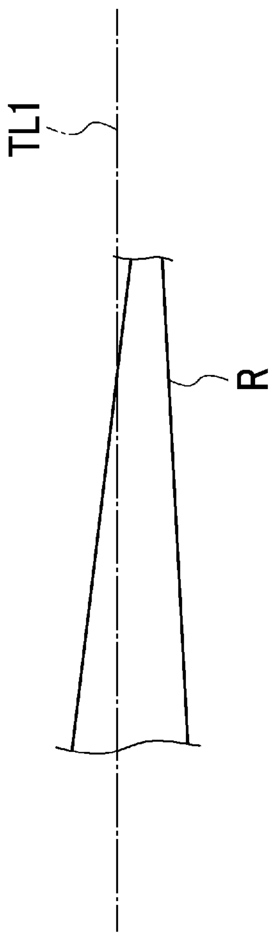
Figure 4C:
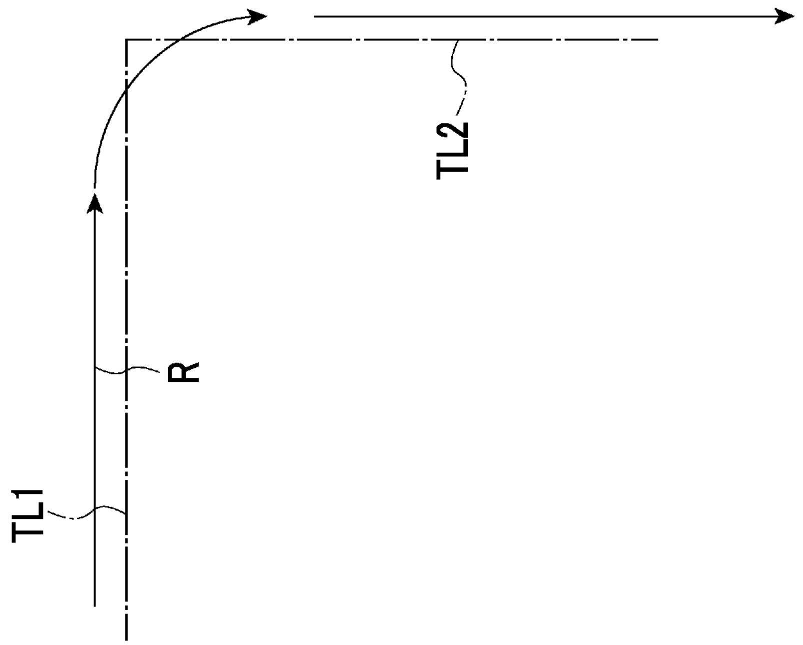

Next, a reference trajectory TL1 of the particle beam R will be described. The reference trajectory TL1 of the particle beam R is a trajectory serving as a reference when the particle beam R moves between the accelerator 2 and the target 10. The reference trajectory TL1 is an advancing direction of the particle beam R, and for example, passes through the center axis of the cylindrical vacuum duct forming a beam transport path. The particle beam R may not completely pass on the reference trajectory TL1 during transport. For example, the particle beam R may slightly bend with respect to the reference trajectory TL1 due to the influence of a fine adjustment by the electromagnets 4 as shown in FIG. 4A while moving along the reference trajectory TL1, or may slightly deviate from the reference trajectory TL1 due to convergence or diffusion of the particle beam R as shown in FIG. 4B. However, as shown in FIG. 4C, when the particle beam R is greatly deflected from the reference trajectory TL1, the particle beam R is transported with reference to a new reference trajectory TL2.

As shown in FIG. 1, in the present embodiment, the reference trajectory TL1 is emitted from the accelerator 2, and reaches the target 10 in a straight line. Therefore, the transport path 9 is composed of a straight pipe extending linearly along the reference trajectory TL1. The transport path 9 is not provided with a bending electromagnet (for example, refer to FIG. 6) for bending the reference trajectory itself from the accelerator 2 to the target 10. However, the transport path 9 may be provided with a bending electromagnet for finely adjusting the particle beam R within a range where the reference trajectory TL1 is not bent.

A local shield 40 (first shield member), an intermediate shield member 41 (second shield member), and a local shield member 42 (second shield member) are provided between the target disposition portion 30 and the accelerator 2. The material of each shield member may be any material as long as the material has a shielding property against radiation, and for example, concrete, lead, iron, polyethylene, boron, or the like may be adopted.

Figure 5:
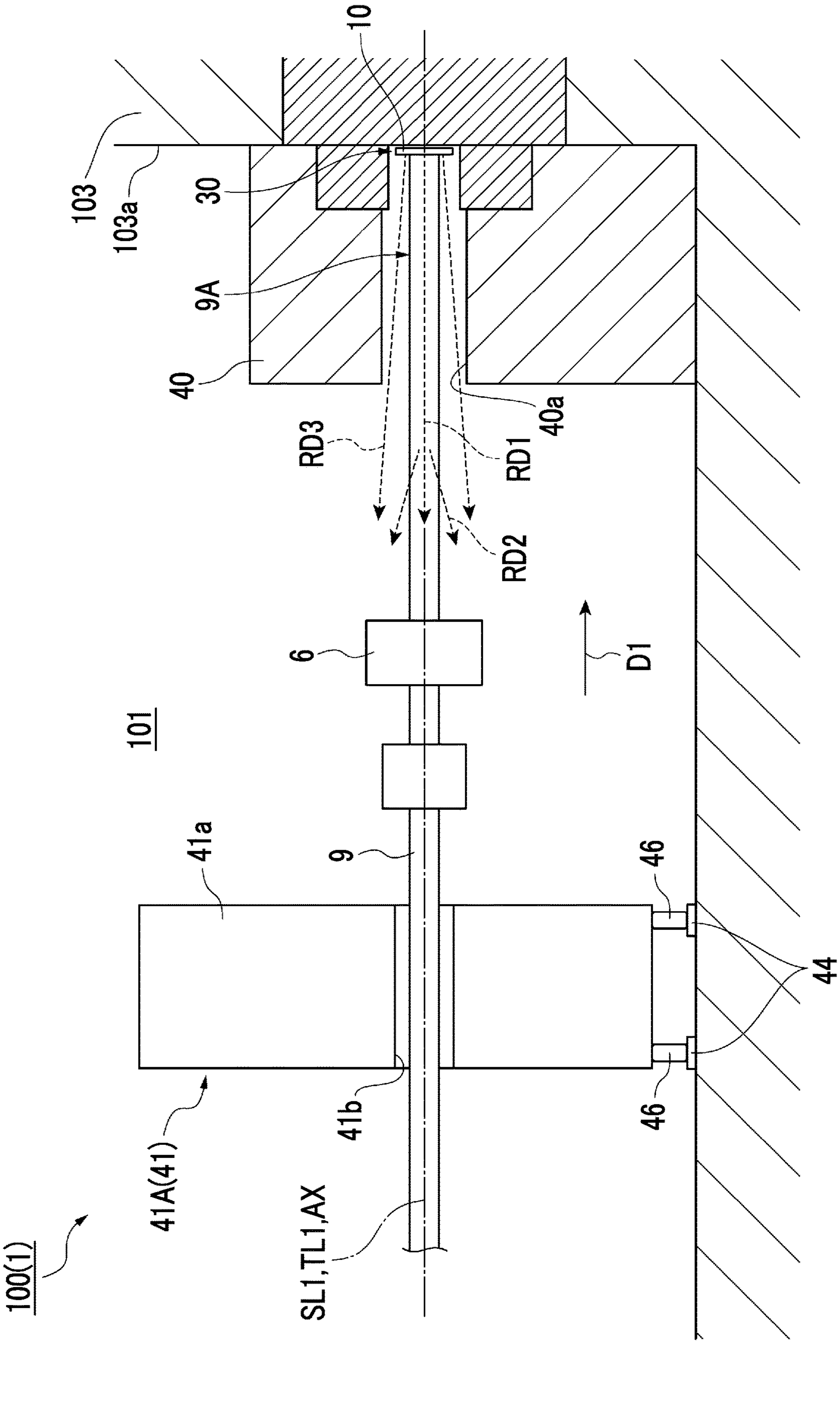
FIG. 5 is a cross-sectional view showing a configuration of the neutron ray generating apparatus in the vicinity of a target.

The local shield 40 is a shield member that shields radiation around the target 10. The local shield 40 is provided on the wall surface 103*a* on the accelerator chamber 101 side of the partition wall 103. As shown in FIG. 5, the local shield 40 is configured by disposing a shield material such as lead so as to have a predetermined thickness from the wall surface 103*a* of the partition wall 103. The local shield is provided with a communication hole 40*a* for passing the transport path 9.

Here, when the target 10 is irradiated with the particle beam R, radiation is generated from the target 10 toward the accelerator chamber 101 side. The radiation is a neutron ray bounced off the target 10, a gamma ray that is secondarily generated, and the like. The radiation is shielded by the local shield 40. However, radiation RD1 shown in FIG. 5 advances opposite to the emission direction D1 inside the transport path 9. When the radiation RD1 exits the local shield 40, the radiation RD1 radiates radiation RD2 that diffuses to the outside of the transport path 9. In addition, part of radiation RD3 generated by the target 10 passes through the communication hole 40*a* and is radiated to the outside of the local shield 40 without being shielded by the local shield 40. In such a manner, the radiation leaking from the local shield 40 is shielded by the intermediate shield member 41 and the local shield member 42.

As shown in FIG. 1, the intermediate shield member 41 is a shield member that shields radiation and that is disposed to be spaced apart from the local shield 40 toward an accelerator 2 side. The intermediate shield member 41 is disposed at a position closer to the target disposition portion 30 between the target disposition portion 30 and the accelerator 2. Namely, the intermediate shield member 41 is provided at a position closer to the target disposition portion 30 than to the accelerator 2 in the emission direction D1. Accordingly, the intermediate shield member 41 can shield radiation leaking from the local shield 40 (refer to FIG. 5) in a preliminary stage before the radiation diffuses throughout the entirety of the accelerator chamber 101. In the present embodiment, the intermediate shield member 41 is disposed on a downstream side in the emission direction D1 with respect to the scanning electromagnet 6.

The intermediate shield member 41 includes a first wall portion 41A and a second wall portion 41B disposed to sandwich the transport path 9 in a horizontal direction (horizontal direction perpendicular to the emission direction D1). The intermediate shield member 41 is movable or removable with respect to an installation position. Namely, each of the wall portions 41A and 41B is movable (refer to an imaginary line) or removable from the installation position indicated by a solid line in FIG. 1, so as to be separated from the transport path 9.

For example, each of the wall portions 41A and 41B has a half-split structure, and may be joined without a gap by aligning joint surfaces 41*a* (refer to FIG. 5) with each other. Here, each of the wall portions 41A and 41B may have a semi-cylindrical communication groove 41*b* (refer to FIG. 5) for passing the transport path 9. As shown in FIG. 5, conveyance paths 44 are provided below the first wall portion 41A, and the first wall portion 41A may move on the conveyance paths 44 via traveling units 46 such as wheels.

The local shield member 42 is disposed at a position closer to the accelerator 2 to locally protect the accelerator 2 between the target disposition portion 30 and the accelerator 2. Namely, the local shield member 42 is provided at a position closer to the accelerator 2 than to the target disposition portion 30 in the emission direction D1. In FIG. 1, the local shield member 42 is provided in front of the accelerator 2. For example, when the accelerator 2 includes a protection object 49 to be protected from radiation, the local shield member 42 is provided at a position where the local shield member 42 covers the protection object 49. Examples of the protection object 49 include an electric component such as a semiconductor (prevention of a malfunction), a resin member used as a support member (prevention of a decrease in support strength), a rubber member used in a seal member (prevention of a decrease in sealing performance), a non-metal material, a member made of heavy metal, and the like. Similarly to the intermediate shield member 41, the local shield member 42 may be movable or removable from the installation position.

Next, actions and effects of the neutron ray generating apparatus 1 and the neutron ray therapy facility 100 according to the present embodiment will be described.

First, a neutron ray therapy facility 200 according to a comparative example will be described with reference to FIG. 6. The neutron ray therapy facility 200 greatly bends the particle beam R generated by the accelerator 2, using a bending electromagnet 201, and transports the particle beam R to the target 10 of the target disposition portion 30. In such a configuration, the accelerator 2 needs to be disposed such that the emission direction D1 of the particle beam R of the accelerator 2 and the reference line SL1 of the transport path 9 are perpendicular to each other. For that reason, the accelerator chamber 101 requires an expansion portion 104 for disposing the accelerator 2. The present inventors have recognized that in this case, the entirety of the neutron ray therapy facility 200 becomes large due to a layout relationship between the accelerator 2 and the transport path 9 for the particle beam R. On the other hand, as simply shown in FIG. 1, when the accelerator 2 is disposed such that the transport path 9 becomes a straight line, there is a possibility that the accelerator 2 is radioactivated due to the influence of radiation leaking from the target 10.

On the other hand, in the neutron ray generating apparatus 1 according to the present embodiment, the accelerator 2 and the target disposition portion 30 are disposed on the reference line SL1 of the transport path 9. In such disposition, the size of the entirety of the apparatus can be reduced compared to disposition in which the trajectory of the particle beam R from the accelerator 2 is greatly bent as shown in FIG. 6 to irradiate the target 10 with the particle beam R. In addition, since the transport path 9 can be shortened, the number of the electromagnets can be reduced as compared to that in FIG. 6. In addition, the local shield 40 that shields radiation and the shield members 41 and 42 that shield radiation and that are disposed to be spaced apart from the local shield 40 toward the accelerator 2 side are provided between the target disposition portion 30 and the accelerator 2. In this case, the shield members 41 and 42 can shield radiation from the target 10 that cannot be completely shielded by the local shield 40. For that reason, even when the accelerator 2 is disposed as described above, radiation toward the accelerator 2 can be shielded by the shield members 41 and 42. As described above, the size can be reduced while suppressing the radioactivation of the accelerator 2.

The transport path 9 may include a first portion 9A (refer to FIG. 5) closer to the target disposition portion 30 than to the accelerator 2, and the reference line SL1 of the first portion 9A may overlap the accelerator 2. In this case, the radiation can be effectively shielded.

The connecting part 33 between the transport path 9 and the accelerator 2 may be disposed to overlap the reference line SL1. In this case, the particle beam R emitted from the connecting part 33 of the accelerator 2 can travel straight toward the target 10 along the reference line SL1. For that reason, the number of components for bending the particle beam R, such as a bending electromagnet, can be reduced.

The shield members 41 and 42 may be movable or removable with respect to the installation positions. In this case, since the shield members 41 and 42 are movable or removable from the installation positions during maintenance, maintainability around the installation positions is improved.

The accelerator 2 may emit the particle beam R using a radio frequency. In this case, since different types of particles are less likely to be mixed in the particle beam R, the quality of the neutron ray N with which the patient is irradiated can be improved. In addition, the need for a bending electromagnet or the like for sorting different types of particles can be eliminated. In more detail, in a direct current (DC) accelerator, not only $H^+$ but also $H^{+2}$ is mixed into the particle beam R. In order to discriminate such mixed particles, the discrimination needs to be performed using a difference between mass-to-charge ratio by providing the bending electromagnet 201 as shown in FIG. 6 and by bending the trajectory. On the other hand, in the accelerator 2 of a direct current (DC) type using a radio frequency, since different types of particles having different mass-to-charge ratios are not mixed, even when the bending electromagnet 201 is not provided, irradiation with the neutron ray N of high quality can be performed.

The local shield member 42 may be disposed at a position closer to the accelerator 2 to locally protect the accelerator 2 between the target disposition portion 30 and the accelerator 2. In this case, the local shield member 42 can locally protect the accelerator 2 by narrowing down a range to be protected in the accelerator 2. Accordingly, the certainty of protection can be improved with a small amount of the shield material.

The intermediate shield member 41 may be disposed at a position closer to the target disposition portion 30 between the target disposition portion 30 and the accelerator 2. In this case, the intermediate shield member 41 can shield radiation leaking from the local shield 40 in a preliminary stage before the radiation spreads in the chamber.

The neutron ray therapy facility 100 includes: the accelerator 2 that emits the particle beam R; the target disposition portion 30 that disposes the target 10 that is irradiated with the particle beam R to generate the neutron ray N; and the transport path 9 that transports the particle beam R between the accelerator 2 and the target disposition portion 30. The accelerator 2 and the target disposition portion 30 are disposed on the reference line SL1 of the transport path 9. The local shield 40 that shields radiation and the shield members 41 and 42 that shield the radiation and that is disposed to be spaced apart from the local shield 40 toward the accelerator 2 side are provided between the target disposition portion 30 and the accelerator 2.

According to the neutron ray therapy facility 100, the same actions and effects as those of the neutron ray generating apparatus 1 described above can be obtained.

The present disclosure is not limited to the above-described embodiment.

For example, the system configurations of the neutron ray generating apparatus 1 and the neutron ray therapy facility 100 described above are merely examples, and can be changed as appropriate.

For example, the reference trajectory may not be a perfect straight line as shown in FIG. 1, and may be bent as appropriate without departing from the concept of the present disclosure. Accordingly, the transport path 9 may be bent as appropriate.

In the transport path 9, the reference line SL1 of the first portion 9A close to the target disposition portion 30 overlaps the accelerator 2. For example, even in a mode where a portion of the transport path 9 on a side closer to the accelerator 2 is bent with respect to a portion of the transport path 9 on a side closer to the target, the reference line SL1 (of an extension line) on the side closer to the target may overlap the accelerator 2, and in this case as well, shielding can be effectively performed.

It should be understood that the invention is not limited to the above-described embodiment, but may be modified into various forms on the basis of the spirit of the invention. Additionally, the modifications are included in the scope of the invention.

What is claimed is:

1. A neutron ray generating apparatus comprising:

an accelerator that emits a particle beam;

a target disposition portion that disposes a target that is irradiated with the particle beam to generate a neutron ray;

a transport path that transports the particle beam between the accelerator and the target disposition portion;

a first shield member that shields radiation; and a second shield member that shields radiation, the second shield member being disposed to be spaced apart from the first shield member toward a side of the accelerator, wherein the accelerator and the target disposition portion are disposed on a reference line of the transport path, and the first shield member and the second shield member are provided between the accelerator and the target disposition portion.

2. The neutron ray generating apparatus according to claim 1, wherein the transport path includes a first portion closer to the target disposition portion than to the accelerator, and a reference line of the first portion overlaps the accelerator.

3. The neutron ray generating apparatus according to claim 1, further comprising:

a connecting part between the transport path and the accelerator, the connecting part being disposed to overlap the reference line.

4. The neutron ray generating apparatus according to claim 1, wherein the first shield member comprises a communication hole for passing the transport path.

5. The neutron ray generating apparatus according to claim 1, wherein the second shield member is movable or removable with respect to an installation position.

6. The neutron ray generating apparatus according to claim 1, wherein the accelerator emits the particle beam using a radio frequency.

7. The neutron ray generating apparatus according to claim 1, wherein the second shield member is disposed at a position closer to the accelerator between the accelerator and the target disposition portion to locally protect the accelerator.

8. The neutron ray generating apparatus according to claim 1, wherein the second shield member is disposed at a position closer to the target disposition portion between the accelerator and the target disposition portion.

9. The neutron ray generating apparatus according to claim 1, further comprising:

a deceleration member that decelerates the neutron ray generated by the target; and a shield member that shields the neutron ray and a gamma ray generated along with generation of the neutron ray so as not to be released to an outside.

10. The neutron ray generating apparatus according to claim 9, wherein the shield member is provided to surround the deceleration member.

11. The neutron ray generating apparatus according to claim 9, wherein the deceleration member has a laminated structure including a layer that mainly decelerates fast neutrons contained in the neutron ray, and a layer that mainly decelerates epithermal neutrons contained in the neutron ray.

12. The neutron ray generating apparatus according to claim 1, further comprising:

a collimator that shapes an irradiation field of the neutron ray.

* * * * *